(12) United States Patent
Tanaka et al.

(10) Patent No.: US 9,895,331 B2
(45) Date of Patent: Feb. 20, 2018

(54) PROPHYLACTIC AND/OR THERAPEUTIC AGENT FOR RADIATION DAMAGE

(71) Applicants: The University of Tokyo, Bunkyo-ku, Tokyo (JP); SBI Pharmaceuticals Co., Ltd., Minato-ku, Tokyo (JP)

(72) Inventors: Tohru Tanaka, Tokyo (JP); Motowo Nakajima, Tokyo (JP); Fuminori Abe, Tokyo (JP); Hidenori Ito, Tokyo (JP); Kiwamu Takahashi, Tokyo (JP); Kouji Matsushima, Tokyo (JP); Satoshi Ueha, Tokyo (JP); Jun Abe, Tokyo (JP)

(73) Assignees: The University of Tokyo, Tokyo (JP); SBI Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 14/415,219

(22) PCT Filed: Jul. 11, 2013

(86) PCT No.: PCT/JP2013/004292
§ 371 (c)(1),
(2) Date: Jan. 16, 2015

(87) PCT Pub. No.: WO2014/017046
PCT Pub. Date: Jan. 30, 2014

(65) Prior Publication Data
US 2015/0190356 A1    Jul. 9, 2015

(30) Foreign Application Priority Data

Jul. 23, 2012 (JP) ................. 2012-163110

(51) Int. Cl.
| | |
|---|---|
| A61K 31/197 | (2006.01) |
| A61K 31/22 | (2006.01) |
| A61K 33/26 | (2006.01) |
| A61K 31/555 | (2006.01) |
| A61K 45/06 | (2006.01) |
| A61K 31/24 | (2006.01) |

(52) U.S. Cl.
CPC ............ *A61K 31/197* (2013.01); *A61K 31/22* (2013.01); *A61K 31/24* (2013.01); *A61K 31/555* (2013.01); *A61K 33/26* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,079,262 A | * | 1/1992 | Kennedy | A61K 31/195 514/145 |
| 5,981,512 A | | 11/1999 | Nowicky | |
| 8,563,605 B2 | | 10/2013 | Miyanari et al. | |
| 2011/0196033 A1 | | 8/2011 | Tanaka | |

FOREIGN PATENT DOCUMENTS

| | | | |
|---|---|---|---|
| JP | 05-039218 A | | 2/1993 |
| JP | 06-145057 A | | 5/1994 |
| JP | 11-505851 A | | 5/1994 |
| JP | 07-165602 A | | 6/1995 |
| JP | 2003-335674 A | | 11/2003 |
| JP | 2004-043391 A | | 11/2003 |
| JP | 2007-512378 A | | 5/2007 |
| JP | 2007-302640 A | | 11/2007 |
| JP | 2009-298739 A | | 12/2009 |
| JP | 2011-016753 A | | 1/2011 |
| JP | 2011-207841 A | | 10/2011 |
| WO | WO 2005/053682 A2 | | 6/2005 |
| WO | WO 2006/033412 A1 | | 3/2006 |
| WO | WO 2009/139156 A1 | | 11/2009 |

(Continued)

OTHER PUBLICATIONS

English translation of JP2011-16753 (2011).*
English translation of JP2009298739.*
Akiba, Suminori, "Radiation and Cancer," Journal of Clinical and Experimental Medicine (Igaku No Ayumi), May 5, 2012, 241(5):327-332, with partial English translation.
Escudero et al., "Chronic x-ray dermatitis treated by topical 5-aminolaevulinic acid-photodynamic therapy," British Journal of Dermatology, 2002, 147:394-396.
Malik et al., "Stimulation of Friend Erythroleukemic Cell Cytodifferentiation by 5-Amino Levulinic Acid; Porphyrins, Cell Size, Segregation of Sialoglycoproteins, and Nuclear Translocation," Exp. Hematol., 1988, 16:330-335.

(Continued)

*Primary Examiner* — Bong-Sook Baek
(74) *Attorney, Agent, or Firm* — Foley & Lardner LLP

(57) ABSTRACT

An object of the present invention is to provide a preventive and/or therapeutic agent for radiation damage that has a novel mechanism of action and can prevent and alleviate a wide range of symptoms of radiation damage for which no therapeutic measures have been available so far, and moreover, is highly safe to humans. A preventive and/or therapeutic agent for radiation damage comprising a compound represented by the following formula (I) such as 5-aminolevulinic acid (5-ALA) or a salt thereof as an active ingredient can be used to improve the survival rate, improve body weight reduction, and alleviate hematopoietic disorder:

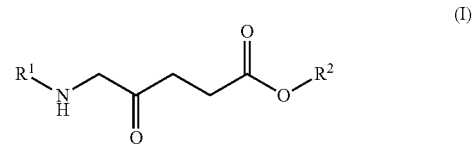

(I)

(wherein $R^1$ represents a hydrogen atom or an acyl group; and $R^2$ represents a hydrogen atom, a linear or branched alkyl group, a cycloalkyl group, an aryl group, or an aralkyl group).

16 Claims, 7 Drawing Sheets

(56) References Cited

FOREIGN PATENT DOCUMENTS

WO     WO 2010/050179 A1     5/2010
WO     WO2013/054755     *     4/2013

OTHER PUBLICATIONS

Miyoshi et al., "PD and PDT with Porphyrin Precursors (5-ALA) in Japan," JJSLSM, 2008, 164-168, with English abstract on first page.
Schulman et al., "The effect of X-irradiation on the biosynthesis of haemoglobin, II. Experiments with δ-aminolevulinic acid-2,3-$^{14}$C," Int. J. Rad. Biol., 1960, 2(1):28-36.
Dover et al., "Topical 5-Aminolevulinic Acid Combined With Intense Pulsed Light in the Treatment of Photoaging," Arch. Dermatol., Oct. 1, 2005, 141(10):1247-1252.
Morokuma et al., "Hair growth stimulatory effect by a combination of 5-aminolevulinic acid and iron ion," International Journal of Dermatology, Dec. 1, 2008, 47(12):1298-1303.

* cited by examiner

[Figure 1]
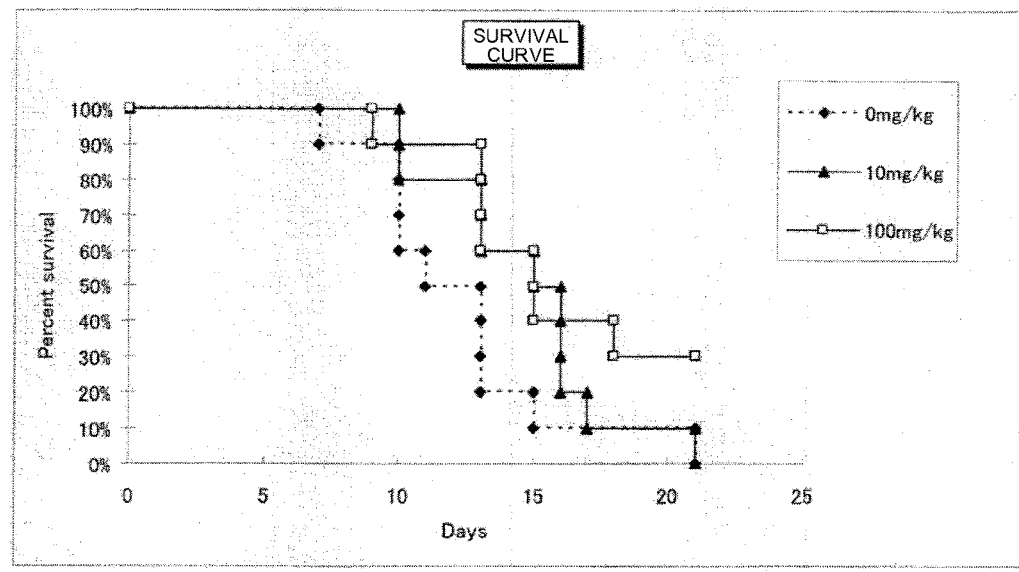
[Figure 2]
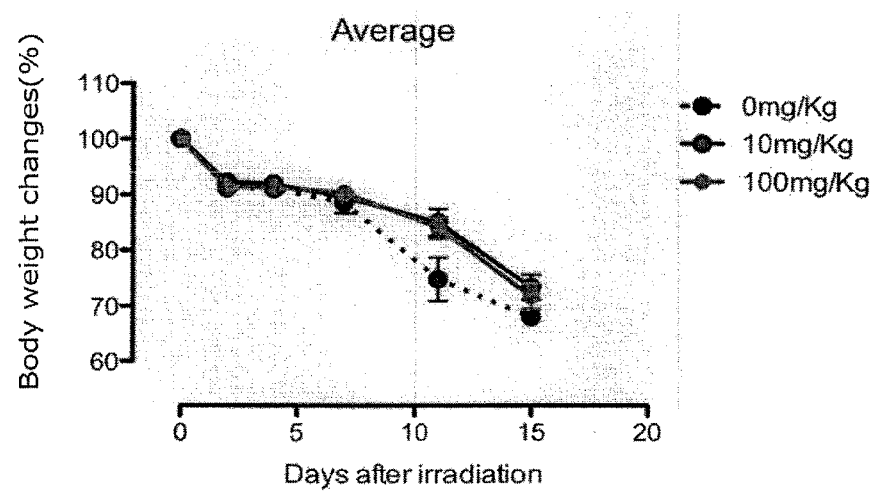

[Figure 3]
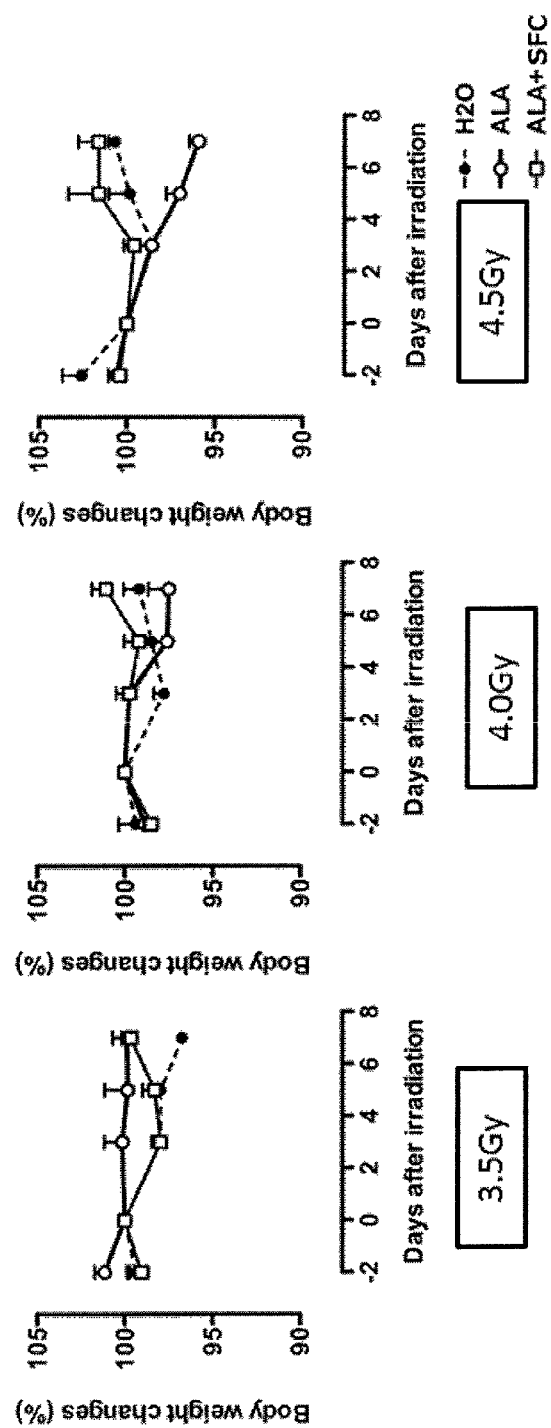

[Figure 4]
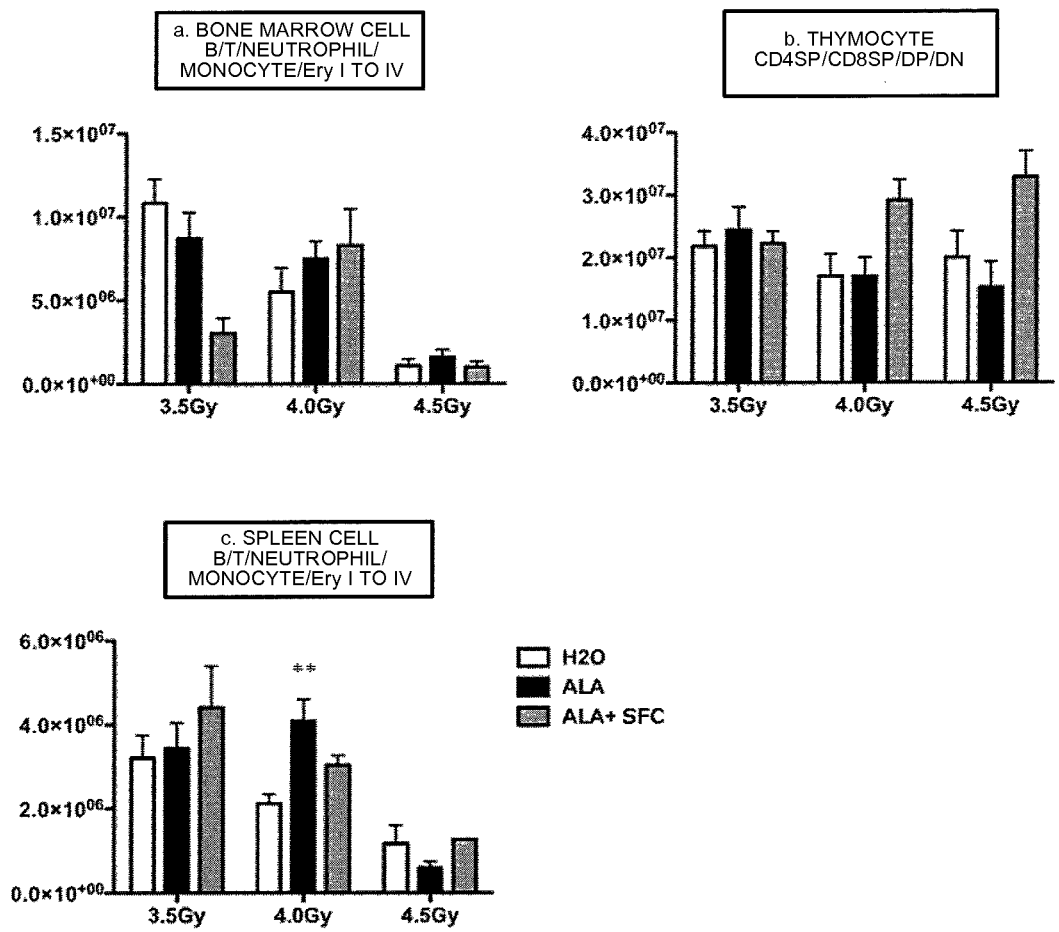

[Figure 5]
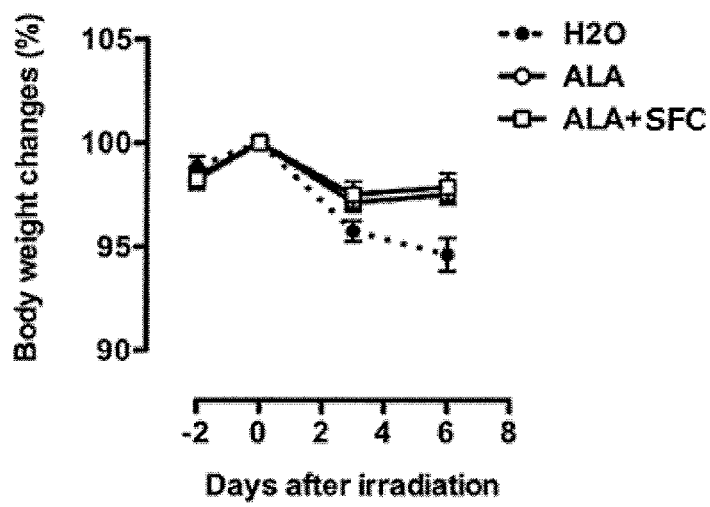
[Figure 6]
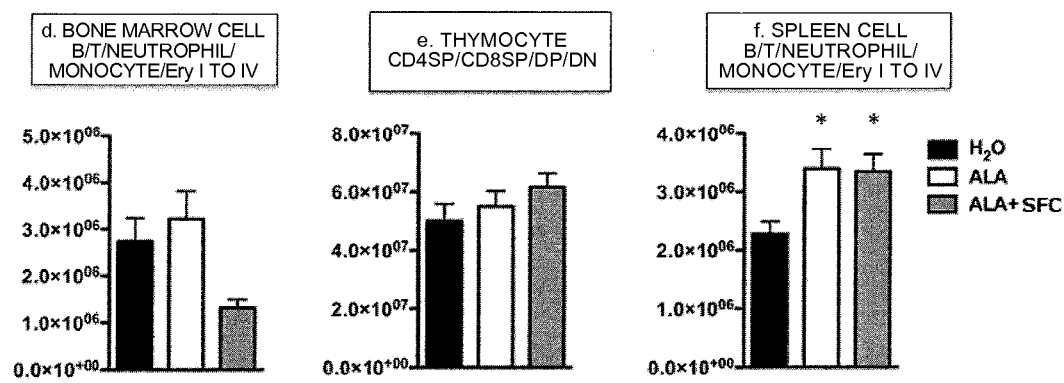

[Figure 7]
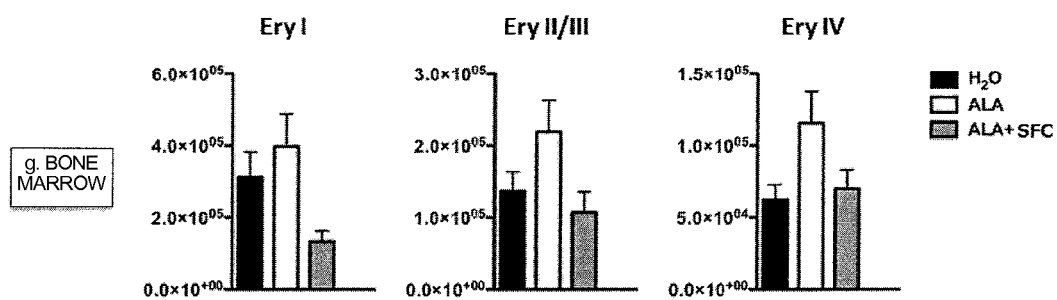
[Figure 8]
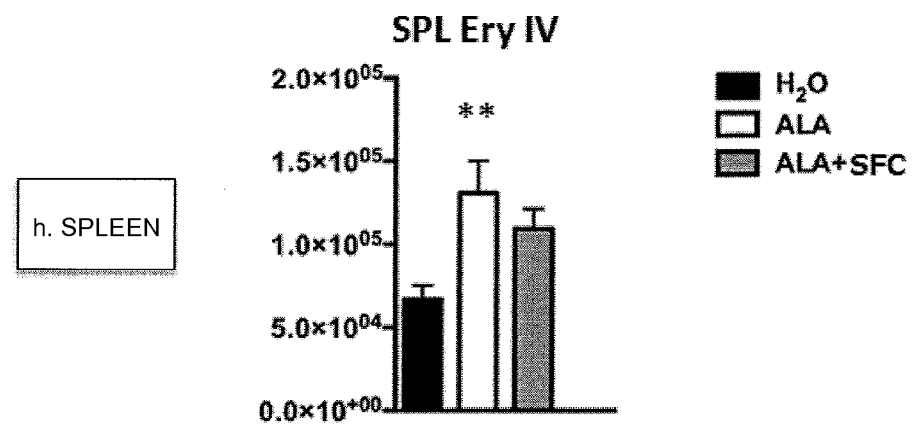

[Figure 9]
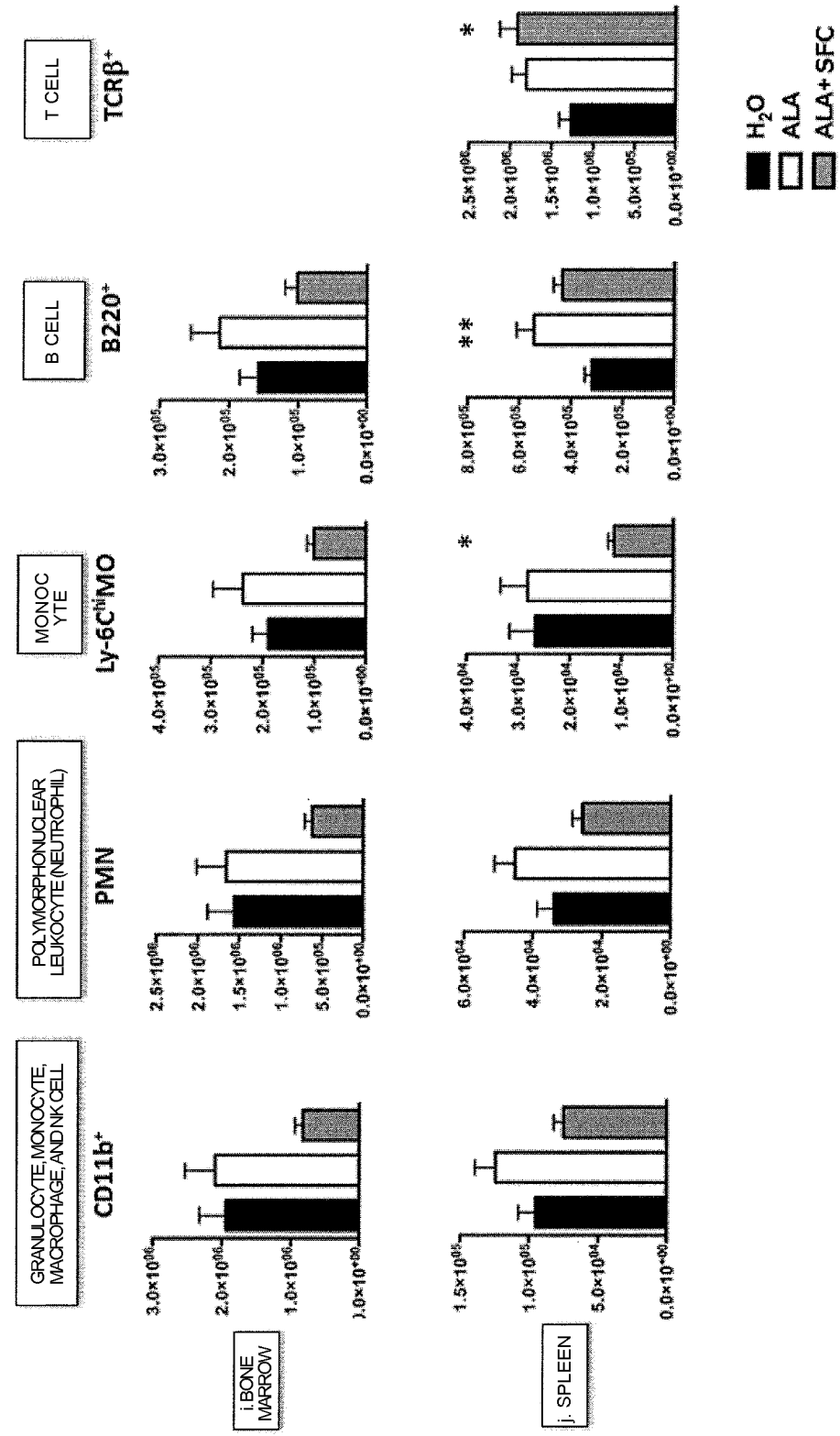

[Figure 10]
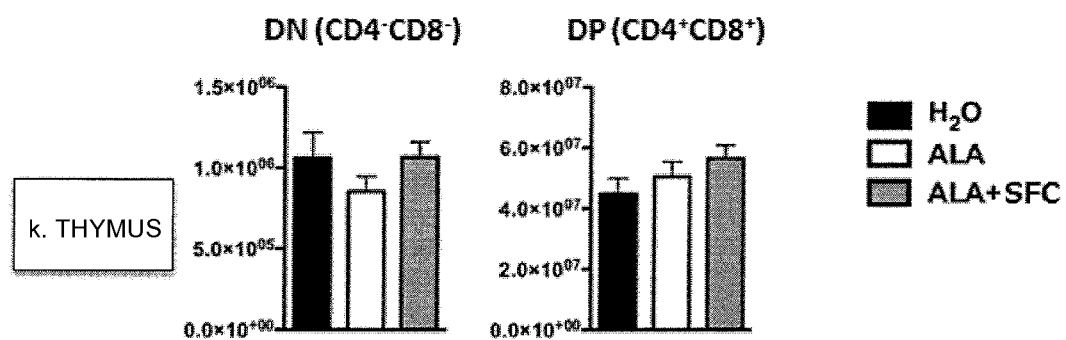

PROPHYLACTIC AND/OR THERAPEUTIC AGENT FOR RADIATION DAMAGE

CROSS-REFERENCE TO RELATED APPLICATIONS

This application is a National Stage application of PCT/JP2013/004292, filed Jul. 11, 2013, which claims priority from Japanese application no JP 2012-163110, filed Jul. 23, 2012.

TECHNICAL FIELD

The present invention relates to a preventive and/or therapeutic agent for radiation damage, in more detail, to a preventive and/or therapeutic agent for radiation damage comprising 5-aminolevulinic acid (5-ALA) or a derivative thereof, or a salt of the 5-ALA or the derivative.

BACKGROUND ART

Radiation damage is a generic term for physical damage or injury caused in organisms by exposure to radiation such as X-ray and gamma ray. As a cause of radiation damage, irradiation, radioactive contamination, and the like are known. Radiation damage occurs as early radiation damage (acute radiation damage), which is radiation damage accompanied by acute phase symptoms that develops right after or within several months of exposure to radiation, or delayed radiation damage (late radiation damage), which is radiation damage that develops several years to several decades after exposure to radiation.

The higher the cell division activity, the higher the sensitivity of the cell to radiation, and the cell renewal system including, for example, hematopoietic organs is most susceptible to radiation. For example, in early radiation damage, exposure to 1 Gy (gray) or more causes symptoms called radiation sickness, which involves symptoms similar to hangover such as nausea, vomiting, and general malaise, in some people. Exposure to 1.5 Gy or more affects hematopoietic cells, which are most susceptible, and the cessation of leucocyte and platelet supply results in increased hemorrhage and reduced immunocompetence, and in severe cases individuals die within about 30 to 60 days. Also, in the skin, in which epithelial basal cells are highly susceptible, by exposure to 3 Gy or more, hair loss and temporary erythema occur, and by exposure to 7 to 8 Gy, blister forms, and by exposure to 10 Gy or more, ulcer is observed. By exposure to 5 Gy or more of radiation, stem cells in the small intestine are killed, leading to the cessation of absorptive cell supply. As a consequence, individuals develop diarrhea due to reduced absorption capacity, or bacterial infection, and in severe cases, die within 20 days. Exposure to an extremely high radiation dose of 15 Gy or more affects the central nerve, causing disturbed consciousness and symptoms of shock. The effect on the central nerve appears quickly, killing most of the irradiated individuals within five days. Meanwhile, in delayed radiation damage, the incidence rates of various types of malignant tumors including leukemia, radiation cataract, and the like are increased.

Currently, as a preventive measure against radiation exposure, prevention of uptake of radioactive substances generated under unusual circumstances such as accidents by, for example, administration of a stable isotope or a chelating agent corresponding to the radioactive substance, is mainly provided to thereby minimize the internal exposure. However, there is no preventive drug for inhibiting, for example, the development of cancer in those who are exposed to radiation on a daily basis such as cabin attendants and radiology technicians. Moreover, no preventive drug for inhibiting side effects in the patients undergoing cancer radiotherapy, who are exposed to a large dose of radiation, has been established yet. Further, as prevention of side effects of radiotherapy, administration of Shi Quan Da Bu Tang, a Chinese traditional medicine, is also known; however, this is not common. The former is intended to minimize radiation exposure per se by preventing the uptake of radioactive substances generated, whereas the latter is intended to inhibit the development of symptoms caused by radiation to which individuals are exposed. As a therapeutic method for radiation exposure, administration of a hematopoiesis-promoting cytokine and bone marrow transplantation are known. These methods are therapeutic methods for bone marrow suppression, which is one of the symptoms of radiation damage caused by the radioactive substances accumulated in the body, or by direct irradiation. Since bone marrow cells are rendered incapable of undergoing normal cell division by radiation damage, cytokines such as G-CSF are administered to the remaining normal cells to promote proliferation and differentiation of blood cells. In severer cases, transplantation of bone marrow cells may be performed.

In addition, as a preventive and/or therapeutic agent for radiation damage, nitroprusside (see Patent Document 1), lactoferrin (see Patent Document 2), 6,10,14,18-tetramethyl-5,9,13,17-nonadecatetraen-2-one (see Patent Document 3), a pyrazolone derivative (see Patent Document 4), the growth factors SCF, IL3, GM-CSF, and IL6 (see Patent Document 5), (±)-N,N'-propylenedinicotinamide (see Patent Document 6), 13-oxygermylpropionic acid (see Patent Document 7), β-lapachone (see Patent Document 8), a phosphorus derivative of alkaloid (see Patent Document 9), and α-D-glucopyranosyl-(1→2)-L-ascorbic acid (see Patent Document 10) have been proposed.

Meanwhile, 5-ALA is known as an intermediate of the tetrapyrrole biosynthetic pathway, which is widely present in animals, plants, and fungi. Normally, 5-ALA is biosynthesized by 5-aminolevulinate synthetase from succinyl CoA and glycine. Photodynamic therapy using 5-ALA (hereinbelow, may also be referred to as "ALA-PDT") is also developed, which is attracting attention as a less invasive therapeutic method that can maintain QOL, and for example, a diagnostic and/or therapeutic agent for tumor prepared with ALA and the like has been reported. Further, 5-ALA is also known to be useful as a preventive or improving agent or a therapeutic agent for adult diseases, cancer, and male infertility (see for example, Patent Documents 11 to 13).

PRIOR ART DOCUMENTS

Patent Documents

Patent Document 1: Japanese unexamined Patent Application Publication No. 2011-207841
Patent Document 2: Japanese unexamined Patent Application Publication No. 2007-302640
Patent Document 3: Japanese unexamined Patent Application Publication No. 2004-43391
Patent Document 4: Japanese unexamined Patent Application Publication No. 2003-335674
Patent Document 5: Japanese unexamined Patent Application Publication No. 7-165602

Patent Document 6: Japanese unexamined Patent Application Publication No. 6-145057

Patent Document 7: Japanese unexamined Patent Application Publication No. 5-39218

Patent Document 8: Japanese unexamined Patent Application Publication (Translation of PCT Application) No. 2007-512378

Patent Document 9: Japanese unexamined Patent Application Publication (Translation of PCT Application) No. 11-505851

Patent Document 10: WO2006/033412

Patent Document 11: WO2010/050179

Patent Document 12: Japanese unexamined Patent Application Publication No. 2011-16753

Patent Document 13: WO2009/139156

SUMMARY OF THE INVENTION

Object to be Solved by the Invention

An object of the present invention is to provide a preventive and/or therapeutic agent for radiation damage, which can solve the following problems associated with preventive and/or therapeutic agents for radiation damage. This preventive and/or therapeutic agent for radiation damage has a novel mechanism of action and can improve, alleviate, and reduce a wide range of symptoms for which no therapeutic measures have been available so far, and moreover, is highly safe to humans.

[1] There has been no preventive measure against damage caused by continuous exposure to a low dose of radiation.
[2] There has been no drug in general use for prevention of side effects of radiotherapy.
[3] With regard to a therapeutic method, it is difficult to secure a certain level of quality of protein preparations, and moreover, protein preparations are expensive. Also, in regard to hematopoietic stem cell transplantation, the presence of a matching donor is not guaranteed; therefore, it cannot be a versatile therapeutic method.
[4] With regard to a therapeutic method, while damage caused in bone marrow can be inhibited by conventional technology, no therapeutic method for other symptoms such as inflammation, hair loss, and diarrhea has been established yet.

Means to Solve the Object

The present inventors speculated that inflammation caused by radiation could be inhibited by administration of 5-ALA. In light of this, they actually administered 5-ALA to an irradiated mouse model. As a result, they found that the survival rate attributable to radiation damage could be improved and body weight reduction could be improved, and moreover, hematopoietic disorder could be alleviated, thereby completing the present invention.

That is, the present invention relates to [1] a preventive and/or therapeutic agent for radiation damage, comprising a compound represented by the following formula (I) or a salt thereof. Other aspects can include a compound represented by the following formula (I) or a salt thereof, which is used for the prevention and/or treatment of radiation damage.

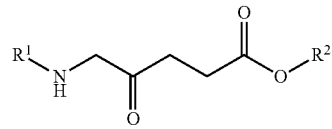

(wherein $R^1$ represents a hydrogen atom or an acyl group; and $R^2$ represents a hydrogen atom, a linear or branched alkyl group, a cycloalkyl group, an aryl group, or an aralkyl group).

The present invention also relates to [2] the preventive and/or therapeutic agent for radiation damage according to [1], wherein $R^1$ and $R^2$ represent a hydrogen atom, [3] the preventive and/or therapeutic agent for radiation damage according to [1] or [2], further comprising an iron compound, [4] the preventive and/or therapeutic agent for radiation damage according to [3], wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide, [5] the preventive and/or therapeutic agent for radiation damage according to any one of [1] to [4], wherein the agent is used for amelioration of body weight reduction, [6] the preventive and/or therapeutic agent for radiation damage according to any one of [1] to [5], wherein the agent is used for improvement in survival rate, and [7] the preventive and/or therapeutic agent for radiation damage according to any one of [1] to [6], wherein the agent is used for alleviation of hematopoietic disorder.

The present invention further relates to [8] a method for preventing and/or treating radiation damage, comprising administering the preventive and/or therapeutic agent for radiation damage according to any one of [1] to [7] to a subject, [9] a kit for preventing and/or treating radiation damage, comprising a) a compound represented by the above formula (I) or a salt thereof; and b) an iron compound, [10] a method for preventing and/or treating radiation damage, comprising administering a) a compound represented by the above formula (I) or a salt thereof; and b) an iron compound simultaneously or one after another to a subject, [11] a combination of preventive and/or therapeutic drugs, comprising a) the preventive and/or therapeutic agent for radiation damage according to any one of [1] to [7]; and b) a preventive and/or therapeutic agent for radiation damage, and [12] a combination of preventive and/or therapeutic drugs, comprising a) a compound represented by the above formula (I) or a salt thereof; b) an iron compound; and c) a preventive and/or therapeutic agent for radiation damage.

Effect of the Invention

The present invention can alleviate, reduce, defend against, improve, prevent, and/or treat radiation damage in a subject. More specifically, the present invention can provide a highly safe preventive and/or therapeutic agent for radiation damage that can increase the survival rate and prevent body weight reduction, and moreover, is expected to alleviate hematopoietic disorder (promote hematopoiesis), which is one of the symptoms of radiation damage, inhibit hair loss, and also, improve deteriorated skin, reduced food and water intake, diarrhea, and reduced activity time, and not only that, improve the posture of a subject who has been exposed to radiation.

BRIEF DESCRIPTION OF DRAWINGS

FIG. 1 is a graph showing the changes in survival rate of a radiation-damaged mouse that was irradiated twice with a radiation dose of 4.0 Gy by administration of 5-ALA hydrochloride.

FIG. 2 is a graph showing the changes in body weight of a radiation-damaged mouse that was irradiated twice with a radiation dose of 4.0 Gy by administration of 5-ALA hydrochloride.

FIG. 3 is a set of graphs each showing the changes in body weight of a radiation-damaged mouse by administration of 5-ALA hydrochloride or 5-ALA hydrochloride+SFC with respect to a radiation dose of 3.5 Gy, 4.0 Gy, or 4.5 Gy.

FIG. 4 is a set of graphs each showing the results of the flow cytometric analysis of the group of cells obtained from the bone marrow, spleen, or thymus of a radiation-damaged mouse administered with 5-ALA hydrochloride or 5-ALA hydrochloride+SFC.

FIG. 5 is a graph showing the changes in body weight of a radiation-damaged mouse irradiated with a radiation dose of 4.0 Gy by administration of 5-ALA hydrochloride or 5-ALA hydrochloride+SFC.

FIG. 6 is a set of graphs each showing the results of the flow cytometric analysis of the group of cells obtained from the bone marrow, spleen, or thymus of a radiation-damaged mouse irradiated with a radiation dose of 4.0 Gy and administered with 5-ALA hydrochloride or 5-ALA hydrochloride+SFC.

FIG. 7 is a set of graphs each showing the results of counting the number of the erythroid progenitor cell Ery I, Ery II/III, or Ery IV among the bone marrow cells of FIG. 6.

FIG. 8 is a graph showing the results of counting the number of the erythroid progenitor cell Ery IV among the spleen cells of FIG. 6.

FIG. 9 is a set of graphs each showing the results of counting the number of polymorphonuclear leukocytes (neutrophils), monocytes, B cells, or CD11b$^+$ cells (top row) among the bone marrow cells of FIG. 6, and the results of counting the number of polymorphonuclear leukocytes (neutrophils), monocytes, B cells, T cells, or CD11b$^+$ cells (bottom row) among the spleen cells of FIG. 6.

FIG. 10 is a set of graphs each showing the results of counting the number of DN or DP among the thymocytes of FIG. 6.

MODE OF CARRYING OUT THE INVENTION

The preventive and/or therapeutic agent for radiation damage of the present invention is not particularly limited as long as the agent comprises a compound represented by the above formula (I) or a salt thereof (hereinafter, they are also collectively referred to as "ALAs") as an active ingredient. The preventive and/or therapeutic agent for radiation damage of the present invention can also comprise an iron compound in addition to ALAs. Further, the preventive and/or therapeutic agent for radiation damage of the present invention is preferably one that can be used to improve the survival rate, improve (prevent) body weight reduction, and alleviate hematopoietic disorder. The preventive and/or therapeutic agent for radiation damage of the present invention can also be used as a pharmaceutical product, a quasi-drug, a cosmetic, a food, a drink, an animal feed, an aquaculture feed, and a pet food. Also, the method for preventing and/or treating radiation damage of the present invention comprises administering the aforementioned preventive and/or therapeutic agent for radiation damage of the present invention to a subject including humans as well as livestock/fowl or pets. Further, the preventive and/or therapeutic agent for radiation damage of the present invention is preferably administered before and after irradiation, for example, every day from 1 to 3 days before irradiation to 5 to 10 days after irradiation.

In the present invention, the "prevention and/or treatment" of radiation damage encompasses reduction of radiation damage, improvement of radiation damage, and alleviation of radiation damage, and the aforementioned radiation damage encompasses early radiation damage and delayed radiation damage.

Also, the kit for preventing and/or treating radiation damage of the present invention is not particularly limited as long as the kit comprises ALAs and an iron compound individually as active ingredients; however, one that can be used to improve survival rate, improve (prevent) body weight reduction, and alleviate hematopoietic disorder is preferable. The method for preventing and/or treating radiation damage of the present invention using the kit for preventing and/or treating radiation damage of the present invention comprises administering ALAs and an iron compound simultaneously or sequentially before and after irradiation to a subject including humans as well as livestock/fowl or pets.

Moreover, the combination of preventive and/or therapeutic drugs of the present invention is not particularly limited as long as the combination comprises the aforementioned preventive and/or therapeutic agent for radiation damage of the present invention and a preventive and/or therapeutic agent for radiation damage other than the preventive and/or therapeutic agent for radiation damage of the present invention or the combination comprises ALAs, an iron compound, and a preventive and/or therapeutic agent for radiation damage. Radiation damage can be prevented and/or treated also by administering these combinations of preventive and/or therapeutic drugs. The preparations (ingredients) of these combinations can be administered simultaneously or separately. Also, the preparations (ingredients) of these combinations can each be administered before and after irradiation, for example, every day from 1 to 3 days before the day of irradiation to 5 to 10 days after the day of irradiation.

Among these ALAs, preferable examples thereof include 5-ALA represented by the formula (I) wherein $R^1$ and $R^2$ each represent a hydrogen atom or a salt thereof. The 5-ALA, also called δ-aminolevulinic acid, is one type of amino acid. Examples of 5-ALA derivatives can include compounds other than 5-ALA, which are represented by the formula (I) wherein $R^1$ represents a hydrogen atom or an acyl group; and $R^2$ represents a hydrogen atom, a linear or branched alkyl group, a cycloalkyl group, an aryl group, or an aralkyl group.

Examples of the acyl group in the formula (I) can include: linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl groups; and aroyl groups having 7 to 14 carbon atoms such as benzoyl, 1-naphthoyl, and 2-naphthoyl groups.

Examples of the alkyl group in the formula (I) can include linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups.

Examples of the cycloalkyl group in the formula (I) can include cycloalkyl groups having 3 to 8 carbon atoms which are saturated or may have a partially unsaturated bond, such as cyclopropyl, cyclobutyl, cyclopentyl, cyclohexyl, cycloheptyl, cyclooctyl, cyclododecyl, and 1-cyclohexenyl groups.

Examples of the aryl group in the formula (I) can include aryl groups having 6 to 14 carbon atoms such as phenyl, naphthyl, anthryl, and phenanthryl groups.

Examples of the aralkyl group in the formula (I) can include aralkyl groups whose aryl moiety is the same as those exemplified above as the aryl group and alkyl moiety is the same as those exemplified above as the alkyl group and can specifically include aralkyl groups having 7 to 15 carbon atoms such as benzyl, phenethyl, phenylpropyl, phenylbutyl, benzhydryl, trityl, naphthylmethyl, and naphthylethyl groups.

The ALA derivative is preferably a compound wherein $R^1$ is, for example, a formyl, acetyl, propionyl, or butyryl group or a compound wherein $R^2$ is, for example, a methyl, ethyl, propyl, butyl, or pentyl group. Preferable examples of combinations of $R^1$ and $R^2$ can include combinations of formyl and methyl, acetyl and methyl, propionyl and methyl, butyryl and methyl, formyl and ethyl, acetyl and ethyl, propionyl and ethyl, and butyryl and ethyl.

It is only required that ALAs should act as an active ingredient in the form of 5-ALA of the formula (I) or its derivative in vivo. ALAs can be administered as various salts, esters, or prodrugs (precursors), which are degradable by enzymes in vivo, in order to enhance solubility according to dosage forms. Examples of the salts of 5-ALA and its derivative can include pharmacologically acceptable acid-addition salts, metal salts, ammonium salts, and organic amine-addition salts. Examples of the acid-addition salts can include: various inorganic acid salts such as hydrochloride, hydrobromide, hydroiodide, phosphate, nitrate, and sulfate; and various organic acid-addition salts such as formate, acetate, propionate, toluenesulfonate, succinate, oxalate, lactate, tartrate, glycolate, methanesulfonate, butyrate, valerate, citrate, fumarate, maleate, and malate. Examples of the metal salts can include: various alkali metal salts such as lithium salt, sodium salt, and potassium salt; various alkaline earth metal salts such as magnesium and calcium salts; and salts of various other metals such as aluminum and zinc. Examples of the ammonium salts can include ammonium salt and alkylammonium salts such as tetramethylammonium salts. Examples of the organic amine salts can include various salts such as triethylamine salt, piperidine salt, morpholine salt, and toluidine salt. These salts may be used in the form of solution.

Of these ALAs, 5-ALA and various esters thereof such as 5-ALA methyl ester, 5-ALA ethyl ester, 5-ALA propyl ester, 5-ALA butyl ester, and 5-ALA pentyl ester, and their hydrochlorides, phosphates, and sulfates are desirable. Particularly preferable examples thereof can include 5-ALA hydrochloride and 5-ALA phosphate.

These ALAs can be produced by any method known in the art such as chemical synthesis, microbial production, or enzymatic production. Also, these ALAs may form a hydrate or a solvate and can be used singly or in appropriate combination of two or more thereof.

The iron compound may be an organic salt or an inorganic salt. Examples of the inorganic salt can include ferric chloride, iron sesquioxide, iron sulfate, and ferrous pyrophosphate. Examples of the organic salt can include: carboxylates, for example, hydroxycarboxylates including citrates such as ferrous citrate, iron sodium citrate, sodium ferrous citrate, and iron ammonium citrate; organic acid salts such as ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, and sodium iron succinate citrate; and heme iron, iron dextran, iron triethylenetetramine, lactoferrin iron, transferrin iron, sodium iron chlorophyllin, ferritin iron, saccharated iron oxide, and iron glycine sulfide. Among them, sodium ferrous citrate or iron sodium citrate is preferable.

These iron compounds may be used singly or as a mixture of two or more thereof. The dose of the iron compound can be 0.01 to 100 parts by mol with respect to 1 part by mol of ALAs (in terms of the dose of 5-ALA) and is desirably 0.05 to 10 parts by mol, more desirably 0.1 to 8 parts by mol, with respect to 1 part by mol of ALAs (in terms of the dose of 5-ALA).

In the method for preventing and/or treating radiation damage using ALAs in combination with an iron compound according to the present invention, ALAs and the iron compound can be administered either as a composition comprising them or each independently simultaneously or sequentially. In the case where ALAs and the iron compound are administered each independently, it is preferred to administer them simultaneously. In the case where ALAs and the iron compound are administered each independently sequentially, it is preferred to administer them so as to produce additive effects, preferably synergistic effects.

The preventive and/or therapeutic agent for radiation damage and the kit for preventing and/or treating radiation damage according to the present invention can be used further in combination with one or more of a hematopoiesis-promoting cytokine, nitroprusside, lactoferrin, 6,10,14,18-tetramethyl-5,9,13,17-nonadecatetraen-2-one, a pyrazolone derivative, the growth factors SCF, IL3, GM-CSF, and IL6, (±)-N,N'-propylenedinicotinamide, 13-oxygermylpropionic acid, β-lapachone, a phosphorus derivative of alkaloid, α-D-glucopyranosyl-(1→2)-L-ascorbic acid, and an existing preventive and/or therapeutic agent for radiation damage such as amifostine. Also, the preventive and/or therapeutic agent for radiation damage and the kit for preventing and/or treating radiation damage according to the present invention can be used in combination with bone marrow transplantation therapy. The preventive and/or therapeutic agent for radiation damage and the kit for preventing and/or treating radiation damage according to the present invention differ in the mechanism of action from the above-mentioned existing preventive and/or therapeutic agents for radiation damage and bone marrow transplantation therapy. Thus, use of the combination of preventive and/or therapeutic drugs for radiation damage of the present invention can be expected to produce additive effects and, in some cases, synergistic effects.

Examples of administration routes for each ingredient in the preventive and/or therapeutic agent for radiation damage, the kit for preventing and/or treating radiation damage, and the combination of preventive and/or therapeutic drugs according to the present invention can include oral administration (including sublingual administration) and parenteral administration such as nasal drip, inhalation, intravenous administration (including drip infusion), transdermal administration using patches or the like, and administration based on suppositories or forced enteral feeding using nasogastric tubes, nasoenteric tubes, gastric fistula tubes, or intestinal fistula tubes. It is to be noted that as the administration route for an existing preventive and/or therapeutic agent for radiation damage in the combination of preventive and/or therapeutic drugs, it is preferred to adopt the administration route that has been already approved for each drug.

The dosage form of each ingredient in the preventive and/or therapeutic agent for radiation damage, the kit for preventing and/or treating radiation damage, and the combination of preventive and/or therapeutic drugs according to the present invention can be appropriately determined according to the administration route. Examples thereof can include injections, nasal drops, intravenous drops, tablets, capsules, fine granules, powders, solutions, liquids in a form dissolved in syrups or the like, patches, and suppositories. Each ingredient in the preventive and/or therapeutic agent for radiation damage and the kit for preventing and/or treating radiation damage according to the present invention may be administered for medical use as well as in the form of supplement tablets or capsules. Particularly, the form of disintegrating tablets that are rapidly disintegrable in the mouth or the form of solutions suitable for nasogastric administration is preferable for elderly people, infants, or the like who have difficulty in swallowing.

The preventive and/or therapeutic agent for radiation damage and the kit for preventing and/or treating radiation damage according to the present invention can be prepared, if necessary, by the addition of pharmacologically acceptable carriers, excipients, diluents, additives, disintegrants, binders, coating agents, lubricating agents, glidants, lubricants, flavoring agents, sweetening agents, solubilizers, solvents, gelling agents, nutrients, etc. Specific examples thereof can include water, saline, animal fat and oil, plant oil, lactose, starch, gelatin, crystalline cellulose, gum, talc, magnesium stearate, hydroxypropylcellulose, polyalkylene glycol, polyvinyl alcohol, and glycerin. In the case of preparing the preventive and/or therapeutic agent for radiation damage of the present invention as an aqueous solution, it should be noted that the aqueous solution is kept from becoming alkaline, in order to prevent the degradation of ALAs. If the aqueous solution becomes alkaline, the degradation of ALAs may be prevented by the removal of oxygen.

The preventive and/or therapeutic agent for radiation damage and the kit for preventing and/or treating radiation damage according to the present invention can be used for humans as well as in the veterinary field including livestock/fowl or pets. When the subject is human, the dose, administration frequency, and administration period of the preventive and/or therapeutic agent differ depending on the age, body weight, symptoms, etc., of a patient with radiation damage. Examples of the dose of ALAs per adult can include 0.01 mmol to 25 mmol/day, preferably 0.025 mmol to 7.5 mmol/day, more preferably 0.075 mmol to 5.5 mmol/day, and even more preferably 0.2 mmol to 2 mmol/day in terms of moles of 5-ALA. Examples of the administration frequency can include one or more dosages per day and continuous administration using drip infusion or the like. The administration period may be determined by a pharmacologist in this technical field or a clinician according to known methods.

Hereinafter, the present invention will be described more specifically with reference to Examples. However, the technical scope of the present invention is not intended to be limited to these examples.

Example 1

<Radiation Damage-Alleviating Effect of Administration of 5-ALA on a Mouse Suffering from Radiation Damage>

In relation to death caused by various symptoms including bone marrow suppression developing in association with irradiation, the survival rate-improving effect, inhibition of body weight reduction, and changes in the appearance by administration of ALA were examined.

Experimental Method (1) Animals and Rearing Conditions

Male 8-week-old C57BL/6 mice were purchased from Japan SLC, Inc. and mice that appeared healthy by visual inspection on the day of arrival were subjected to the test. On the day after arrival, based on the body weight, the mice were divided into three groups of 10 mice per group by random sampling, and further, one group was divided into three, three, and four mice per cage. The mice were allowed to feed on the basic feed MF manufactured by Oriental Yeast Co., Ltd. and tap water ad libitum and reared in a rearing room at a room temperature of 23 to 24° C., a humidity of 30 to 40%, and under 12 hours of fluorescent lamp lighting.

(2) Test Groups

The mice were divided into three groups of [1] to [3], each receiving a different drug, as shown below. Group [1]; Non-5-ALA administration group (10 mice) Group [2]; 5-ALA hydrochloride 10 mg/kg body weight administration group (10 mice) Group [3]; 5-ALA hydrochloride 100 mg/kg body weight administration group (10 mice)

(3) Induction of Radiation Damage

Using Pantac HF350 (200 KV, 20 mA Filter: Cu 0.1 mm+Al 0.5 mm), the mice were irradiated with 4 Gy of radiation twice at a 3-hour interval (a total of 8 Gy).

(4) Drug Administration

After initiation of irradiation, water was forcedly administered to the aforementioned group [1], and an aqueous solution of 5-ALA hydrochloride was forcedly administered to the aforementioned groups [2] and [3] every day in the stomach through a feeding tube.

(5) Measurement of Survival Rate

Setting the day of irradiation at day 0, survival up to day 21 was checked. A mouse that survived for 21 days was judged as alive. During days 5 to 12, the death of the mice was checked at least once every two days, and a mouse exhibiting a 30% or more reduction in body weight, dull movement (unable to escape even when touched), and low body temperature was judged as dead. A mouse that was found to have passed rigor mortis was judged as being dead for 12 hours or longer. Also, when the death was confirmed in the morning hours, the death was judged to have occurred on the previous day.

(6) Measurement of Body Weight

At the time of confirmation of survival in (5) above, body weight was simultaneously measured.

(7) Changes in Appearance

During the measurement in (5) above, it was examined whether there was any change in appearance between the administration group and non-administration group.

[Results]
(1) Changes in Survival Rate

Changes in the survival rate of the test groups used in the examination are shown in FIG. 1. As a result of a significance test between [3] the 100 mg/kg administration group and [1] the non-ALA administration group by the Logrank method, the survival rate was significantly improved in [3] the 100 mg/kg administration group ([1] 0 mg/kg vs. [3] 100 mg/kg; p=0.0289, [1] 0 mg/kg vs. [2] 10 mg/kg; p=0.161).

(2) Changes in Body Weight

Changes in the body weight of the test groups used in the examination are shown in FIG. 2. Eleven days after irradiation, there was a significant difference in the body weight between [1] the non-ALA administration group, and [2] the 10 mg/kg administration group and [3] the 100 mg/kg administration group ([1] 0 mg/kg vs. [3] 100 mg/kg; p=0.03456, [1] 0 mg/kg vs. [2] 10 mg/kg; p=0.03556).

(3) Changes in Appearance

The findings on the changes in the appearance of the test groups used in the examination are shown in the following Table 1. As a result of continuous observation of the appearance of the 5-ALA administration group and non-5-ALA administration group over time, [1] the non-ALA administration group appeared debilitated with lusterless fur and piloerection due to radiation, whereas [2] the 10 mg/kg administration group and [3] the 100 mg/kg administration group exhibited milder piloerection than [1] the non-ALA administration group.

TABLE 1

| | Non-ALA administration group (0 mg/kg) | ALA administration group (10, 100 mg/kg) |
|---|---|---|
| Condition of fur | Appeared debilitated with piloerection | Milder piloerection and debilitation than the control group |

Example 2

<Hematopoiesis-Promoting Effect of Administration of 5-ALA or 5-ALA+Sodium Ferrous Citrate (SFC) on a Mouse Suffering from Radiation Damage>

It was examined whether the hematopoiesis-promoting effect on hematopoietic disorder, which is a side effect of radiotherapy, could be brought about by preventive and/or therapeutic administration of 5-ALA or 5-ALA+SFC.

1. A Test for Studying the Establishment of an Assessment Model

Experimental Method (1) Animals and Rearing Conditions

Male 8-week-old C57BL/6 mice were purchased from Japan SLC, Inc. and mice that appeared healthy by visual inspection on the day of arrival were subjected to the test. On the day after arrival, based on the body weight, the mice were divided into 10 groups of four mice per group by random sampling, and each group was kept in one cage. The mice were allowed to feed on the basic feed MF manufactured by Oriental Yeast Co., Ltd. and tap water ad libitum and reared in a rearing room at a room temperature of 23 to 24° C., a humidity of 30 to 40%, and under 12 hours of fluorescent lamp lighting.

(2) Test Groups

The mice were divided into 10 groups, including nine groups of 1) to 9), each receiving a different drug and exposed to a different radiation dose, and an untreated group, as shown below.

Groups 1) to 3); Three non-5-ALA administration groups, each irradiated with 3.5 Gy, 4.0 Gy, or 4.5 Gy Groups 4) to 6); Three 5-ALA hydrochloride 100 mg/kg body weight administration groups, each irradiated with 3.5 Gy, 4.0 Gy, or 4.5 Gy Groups 7) to 9); Three 5-ALA hydrochloride 100 mg+SFC 157 mg/kg body weight administration groups, each irradiated with 3.5 Gy, 4.0 Gy, or 4.5 Gy (3) Induction of Radiation Damage Using Pantac HF350 (200 KV, 20 mA Filter: Cu 0.1 mm+Al 0.5 mm), the mice were collectively irradiated with three different radiation doses of 3.5 Gy, 4.0 Gy, and 4.5 Gy on day 0.

(4) Drug Administration

From two days before initiation of irradiation (day −2) to day 6, water was forcedly administered to the aforementioned groups 1) to 3), an aqueous solution of 5-ALA hydrochloride was forcedly administered to the aforementioned groups 4) to 6), and an aqueous solution of 5-ALA hydrochloride and SFC was forcedly administered to the aforementioned groups 7) to 9) every day in the stomach through a feeding tube.

(5) Measurement of Body Weight

Setting the day of irradiation at day 0, the body weight was measured two days before initiation of irradiation (day −2), and on day 0, day 3, day 5, and day 7.

(6) Measurement of Blood Cell Count

The group of cells obtained from the bone marrow, spleen, and thymus were analyzed by a flow cytometer. As an index for identifying each cell, the markers shown in the following [Table 2] were each used.

TABLE 2

| Cell type | | Marker |
|---|---|---|
| B cell | | B220[+] |
| T cell (bone marrow and spleen) | | TCRβ[+] |
| Polymorphonuclear leukocyte (neutrophil) | | PMN |
| Monocyte (MO) | | Ly-6C[hi] |
| Erythroid progenitor cell | Immature ↓ Mature | Ery I[*1] Ery II, III Ery IV | CD11b[−]CD71[+]TER119[−] CD11b[−]CD71[+]TER119[+] CD11b[−]CD71[−]TER119[+] |
| T cell (only thymus) | Immature ↓ Mature | DN (double negative)[*2] DP (double positive) CD4SP (CD4single positive) CD8SP (CD8single positive) | CD45[+]CD4[−]CD8[−] CD45[+]CD4[+]CD8[+] CD45[+]CD4[+]CD8[−] CD45[+]CD4[−]CD8[+] |
| Granulocyte, monocyte, macrophage, and NK cell | | CD11b[+] |

[*1]Ery I to IV are erythroid progenitor cells. After sorting only CD11b[−] cells by a flow cytometer, the cells were developed with the two markers for Ter119 and CD71. The expression level of Ter119 increases, while that of CD71 decreases as differentiation proceeds. That is, Ery I is the most immature erythroid progenitor cell, while Ery IV is the most mature erythroid progenitor cell.
[*2]DN, DP, CD4SP, and CD8SP are T cells and progenitor cells of T cells. DN is transformed into DP as differentiation proceeds, and eventually differentiated into CD4SP or CD8SP, both of which are mature T cells. For the distinction between these cells, after sorting only the hemocyte lineage marker CD45[+] cells by a flow cytometer, the cells were developed with the two markers for CD4 and CD8.

[Results]
(1) Changes in Body Weight

Changes in the body weight of the test groups used in a test for studying the establishment of an assessment model are shown in FIG. 3 for radiation doses of 3.5 Gy, 4.0 Gy, and 4.5 Gy. As a result, the body weight reduction by irradiation was within 5% with any radiation dose; however, compared to the H₂O control, alleviation of body weight reduction was observed in the ALA+SFC administration group with any radiation dose.

(2) Measurement of Blood Cell Count

The results of analyzing the group of cells obtained from the bone marrow, spleen, and thymus by a flow cytometer are shown in FIG. 4. The number of bone marrow cells was counted as a sum of B cells, T cells, polymorphonuclear leukocytes (neutrophils), monocytes, and Ery I to IV. The number of thymocytes was counted as a sum of the number of CD4SP, CD8SP, DN, and DP. The number of spleen cells was counted as a sum of B cells, T cells, polymorphonuclear leukocytes (neutrophils), monocytes, and Ery I to IV.

Taking a look at the bone marrow cell count (normally $1.4 \times 10^7$), the threshold is assumed to lie between irradiation with 4.0 Gy and 4.5 Gy. Although the thymocyte count (normally $1.0 \times 10^8$) was decreased to about 1/10 of normal count by irradiation with 3.5 Gy, there was no major gap among irradiation with 3.5 to 4.5 Gy. The spleen cell count (normally $7.5 \times 10^7$) was about 1/30 of normal count by irradiation with 3.5 Gy, and there was a tendency of radiation dose-dependent, linear decrease from irradiation with 3.5 to 4.5 Gy. Also, compared to the H₂O control group, a significant improvement was noted in the spleen cell count in the 4.0 Gy-irradiated, ALA administration group. There was no significant difference in other items. Then, determining that moderate hematopoietic disorder is induced but a stable improvement tendency is observed in each organ by administration of ALA at a radiation dose of 4.0 Gy, the following assessment test for the hematopoiesis-promoting effect was carried out.

2. Assessment Test for Hematopoiesis-Promoting Effect

Experimental Method (1) Animals and Rearing Conditions

Male 8-week-old C57BL/6 mice were purchased from Japan SLC, Inc. and mice that appeared healthy by visual inspection on the day of arrival were subjected to the test. On the day after arrival, based on the body weight, the mice were divided into three groups of eight mice per group by random sampling, and further, one group was divided into four mice per cage. Also, as an untreated group, one group of four mice was kept in one cage. The mice were allowed to feed on the basic feed MF manufactured by Oriental Yeast Co., Ltd. and tap water ad libitum and reared in a rearing room at a room temperature of 23 to 24° C., a humidity of 30 to 40%, and under 12 hours of fluorescent lamp lighting.

(2) Test Groups

The mice were divided into four groups, including three groups a) to c), each receiving a different drug, and an untreated group, as shown below.

Group a); Non-5-ALA administration group

Group b); 5-ALA hydrochloride 100 mg/kg body weight administration group

Group c); 5-ALA hydrochloride 100 mg+SFC 157 mg/kg body weight administration group (3) Induction of Radiation Damage Using Pantac HF350 (200 KV, 20 mA Filter: Cu 0.1 mm+Al 0.5 mm), the mice were collectively irradiated with a radiation dose of 4.0 Gy on day 0.

(4) Drug Administration

From two days before initiation of irradiation (day −2) to day 6, water was forcedly administered to the aforementioned group a), an aqueous solution of 5-ALA hydrochloride was forcedly administered to the aforementioned group b), and an aqueous solution of 5-ALA hydrochloride and SFC was forcedly administered to the aforementioned group c) every day in the stomach through a feeding tube.

(5) Measurement of Body Weight

Setting the day of irradiation at day 0, the body weight was measured two days before initiation of irradiation (day −2), and on day 0, day 3, and day 6.

(6) Measurement of Blood Cell Count

The group of cells obtained from the bone marrow, spleen, and thymus were analyzed by a flow cytometer. As an index for identifying each cell, the markers shown in the above [Table 2] were each used.

[Results]

(1) Measurement of Body Weight

Changes in the body weight of the test groups used in the assessment test for the hematopoiesis-promoting effect are shown in FIG. 5. As a result, it was found that the ALA+SFC administration group exhibited a stable tendency of improvement in body weight reduction.

(2) Measurement of Blood Cell Count

The results of analyzing the group of cells obtained from the bone marrow, spleen, and thymus by a flow cytometer are shown in FIG. 6. The number of bone marrow cells was counted as a sum of B cells, T cells, polymorphonuclear leukocytes (neutrophils), monocytes, and Ery I to IV. The number of thymocytes was counted as a sum of the number of CD4SP, CD8SP, DN, and DP. The number of spleen cells was counted as a sum of B cells, T cells, polymorphonuclear leukocytes (neutrophils), monocytes, and Ery I to IV.

As understood from FIG. 6, compared to the H₂O control group, there was a significant improvement in the spleen cell count in the ALA administration group and the ALA+SFC administration group.

The results of counting the number of the erythroid progenitor cells Ery I, Ery II/III, and Ery IV among the bone marrow cells of FIG. 6 are shown in FIG. 7. As a result, there was a tendency of improvement in the number of bone marrow TER119+erythroid progenitor cells in the ALA administration group. Also, the results of counting the number of the erythroid progenitor cell Ery IV among the spleen cells of FIG. 6 are shown in FIG. 8. As a result, the number of the erythroid progenitor cell Ery IV was improved with statistical significance in the ALA administration group.

Among the bone marrow cells of FIG. 6, the number of each of polymorphonuclear leukocytes (neutrophils), monocytes, and B cells was counted, and the number of CD11b⁺ cells, which are a marker of granulocytes, monocytes, macrophages, and NK cells, was also counted. The results are shown in FIG. 9 (top row). As a result, there was a tendency of improvement in the number of monocytes and B cells in the ALA administration group.

Among the spleen cells of FIG. 6, the number of each of polymorphonuclear leukocytes (neutrophils), monocytes, B cells, and T cells was counted, and the number of CD11b⁺ cells, which are a marker of granulocytes, monocytes, macrophages, and NK cells, was also counted. The results are shown in FIG. 9 (bottom row). There was a tendency of improvement in the number of polymorphonuclear leukocytes, CD11b⁺ cells, and T cells in the ALA administration group. Also, there was a statistically significant improvement in the number of B cells in the ALA administration group. Although there was a statistically significant improvement in the number of T cells in the ALA+SFC administration group, there was a statistically significant decrease in the number of monocytes in the ALA+SFC administration group.

Among the thymocytes of FIG. 6, the number of DN and DP was counted. The results are shown in FIG. 10.

As shown above, a reduction in the spleen cells of a mildly radiation-damaged mouse was inhibited by the administration of ALA and ALA+SFC. Also, among the spleen cells of a mildly radiation-damaged mouse, a reduction in the relatively mature erythroid progenitor cell Ery IV was inhibited by the administration of ALA. By these results, it was suggested that hematopoietic disorder caused by irradiation could be alleviated by the administration of ALA and ALA+SFC.

INDUSTRIAL APPLICABILITY

The preventive and/or therapeutic agent for radiation damage of the present invention can be advantageously used in, for example, the medical field.

The invention claimed is:

1. A method for treating radiation-induced hematopoietic cell death in a subject in need thereof, comprising administering to the subject a therapeutic agent comprising a compound represented by the following formula (I) or a salt thereof:

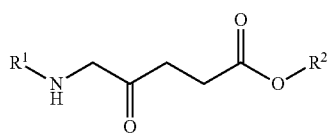

wherein $R^1$ represents a hydrogen atom or an acyl group; and $R^2$ represents a hydrogen atom, a linear or branched alkyl group, a cycloalkyl group, an aryl group, or an aralkyl group; wherein the radiation is X-ray or gamma ray radiation; and wherein the agent is administered by a route selected from the group consisting of oral administration, nasal drip, inhalation, intravenous administration, suppositories, administration though a nasogastric tube, administration through a nasoenteric tube, administration through a gastric fistula tube, and administration through an intestinal fistula tube, wherein administration of the compound promotes hematopoiesis in the subject.

2. The method according to claim 1, wherein $R^1$ and $R^2$ represent a hydrogen atom.

3. The method according to claim 1, wherein the therapeutic agent further comprises an iron compound.

4. The method according to claim 3, wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

5. The method according to claim 1, wherein the subject is a subject in need of amelioration of body weight reduction.

6. The method according to claim 1, wherein the subject is a subject in need of improvement in survival rate.

7. The method according to claim 2, wherein the therapeutic agent further comprises an iron compound.

8. The method according to claim 7, wherein the iron compound is one or more compounds selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

9. The method according to claim 2, wherein the subject is a subject in need of amelioration of body weight reduction.

10. The method according to claim 3, wherein the subject is a subject in need of amelioration of body weight reduction.

11. The method according to claim 4, wherein the subject is a subject in need of amelioration of body weight reduction.

12. The method according to claim 1, wherein the subject is a subject in need of amelioration of body weight reduction and improvement in survival rate.

13. The method according to claim 2, wherein the subject is a subject in need of improvement in survival rate.

14. The method according to claim 3, wherein the subject is a subject in need of improvement in survival rate.

15. The method according to claim 4, wherein the subject is a subject in need of improvement in survival rate.

16. A method for treating radiation-induced hematopoietic cell death in a subject in need thereof, comprising administering to the subject
 (a) a compound represented by the following formula (I) or a salt thereof:

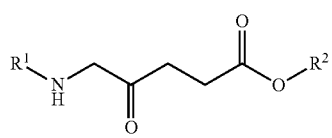

wherein $R^1$ represents a hydrogen atom or an acyl group; and $R^2$ represents a hydrogen atom, a linear or branched alkyl group, a cycloalkyl group, an aryl group, or an aralkyl group; and
 (b) an iron compound simultaneously or one after another to the subject, wherein the radiation is X-ray or gamma ray radiation; and wherein the agent is administered by a route selected from the group consisting of oral administration, nasal drip, inhalation, intravenous administration, suppositories, administration though a nasogastric tube, administration through a nasoenteric tube, administration through a gastric fistula tube, and administration through an intestinal fistula tube, wherein administration of the compound promotes hematopoiesis in the subject.

* * * * *